United States Patent
Roberts (10) Patent No.: US 11,147,895 B1
(45) Date of Patent: Oct. 19, 2021

(54) CPAP EQUIPMENT SANITIZING SYSTEM

(71) Applicant: Exceleron Medical, LLC., St. Paul, MN (US)

(72) Inventor: Keith Roberts, St. Paul, MN (US)

(73) Assignee: Exceleron Medical, LLC, St. Paul, MN (US)

( * ) Notice: Subject to any disclaimer, the term of this patent is extended or adjusted under 35 U.S.C. 154(b) by 198 days.

(21) Appl. No.: 16/366,952

(22) Filed: Mar. 27, 2019

Related U.S. Application Data (60) Provisional application No. 62/648,797, filed on Mar. 27, 2018.

(51) Int. Cl.
*A61L 2/20* (2006.01)
*A61M 16/06* (2006.01)
*A61M 16/16* (2006.01)

(52) U.S. Cl.
CPC ........... *A61L 2/202* (2013.01); *A61L 2202/11* (2013.01); *A61L 2202/24* (2013.01); *A61M 16/06* (2013.01); *A61M 16/16* (2013.01); *A61M 2209/10* (2013.01)

(58) Field of Classification Search
CPC .. A61L 2/202; A61L 2202/24; A61L 2202/11; A61M 16/06; A61M 16/16; A61M 2209/10
See application file for complete search history.

(56) References Cited

U.S. PATENT DOCUMENTS

| | | | |
|---|---|---|---|
| 6,134,806 A * | 10/2000 | Dhaemers | F26B 21/00 34/404 |
| 9,610,373 B2 | 4/2017 | Leyva | |
| 9,616,147 B2 | 4/2017 | Leyva | |
| 9,669,124 B2 | 6/2017 | Leyva | |
| 2002/0063129 A1* | 5/2002 | Potter | B29C 66/61 220/4.13 |
| 2013/0239994 A1* | 9/2013 | Przyjemski | B08B 9/0321 134/22.12 |
| 2016/0250366 A1 | 9/2016 | Leyva | |
| 2018/0311391 A1* | 11/2018 | Leyva | A61L 9/015 |

OTHER PUBLICATIONS

SoClean Product Home Page; www.soclean.com as of Jun. 19, 2019, 5 pgs.
VirtuClean Product Home Page; www.virtuclean.com as of Jun. 19, 2019, 8 pgs.

* cited by examiner

*Primary Examiner* — Sean E Conley
*Assistant Examiner* — Brendan A Hensel
(74) *Attorney, Agent, or Firm* — Michael A. Bondi; Moss & Barnett (57) ABSTRACT

A CPAP equipment sanitizing system that includes an oxidizing gas generator, a sanitizing chamber and tubing. The oxidizing gas generator has an outlet port. The sanitizing chamber includes an enclosure, a fitting and a closure mechanism. The enclosure has an opening. The enclosure is adapted to receive CPAP equipment. The enclosure has an aperture formed in a surface thereof. The fitting that extends through the aperture and sealingly engages the sanitizing chamber. The closure mechanism is capable of substantially closing the opening. The tubing operably attaches the outlet port on the oxidizing gas generator and the fitting.

13 Claims, 9 Drawing Sheets

CPAP EQUIPMENT SANITIZING SYSTEM

REFERENCE TO RELATED APPLICATION

This application claims priority to Provisional Applic. No. 62/648,797, filed on Mar. 27, 2018, the contents of which are incorporated herein by reference.

FIELD OF THE INVENTION

The invention relates generally to a system for cleaning medical equipment. More particularly, the invention relates to a CPAP equipment sanitizing system.

BACKGROUND OF THE INVENTION

Infection within the medical industry is a great concern for care providers, consumers and patients, not to mention infection within society as a whole. Medical devices and instrumentation often require sanitizing, disinfection, washing, cleaning and sterilization between use. Medical devices which circulate atmospheric air or gas to a patient such as a ventilator, oxygen concentrator or continuous positive airway pressure machine in particular, put users and patients of such instruments at a high risk of infections. Infections from such medical devices occur from a multitude of sources, including bacteria, mold, hard to kill spore forming bacteria such as *Bacillus subtillus*, yeast, fungi and viruses.

Ventilator associated pneumonia (VAP) is the leading cause of morbidity and mortality in intensive care units. The occurrence of VAP ranges from 7-70% and the mortality rates range from 20-75% according to a study population. Colonized pathogens can be aspirated from the oropharynx and gastrointestinal tract. Cleaning gas pathways and delivering bacteria and viral free gas within such ventilators is critical to patient well-being and healthcare costs. Ventilator associated pneumonia and infection control Ann Clin Microbiol Antimicrob. 2006; 5: 7. Published online 2006 Apr. 6. doi: 10.1186/1476-0711-5-7 PMCID: PMC1540438.

Ozone is a gas that contains 3 molecules of oxygen. It has been used for years in applications such as treatment of municipal water and bottled water. Ozone has a long history of use in the disinfection of water since 1893. Ozone has been used as a food preservative since 1909 and in 1939 it was recognized that it prevented the growth of yeast and mold during the storage of fruits.

Ozone has a broad use for microbialcidal applications and is effective at killing viruses, bacteria, biofilms, fungi, spore formers such as *bacillus subtillus* and protozoa. The further benefit of ozone is that these microbes are not able to build resistance to ozone because ozone oxidates the microbes and destroys them mechanically. Microbes do not become oxidation-resistant.

Ozone gas is created by an electrical charge or from oxygen using a similar process. Ozone survives in the atmosphere for short periods of time before it is decomposed into oxygen and water. Ozone is reportedly more environmentally friendly than chlorine gas and chlorinated sanitizers. The end product of ozone does not leave a residue on surfaces and makes an ideal disinfectant for many applications.

Sleep apnea is a condition where a person's airway becomes obstructed during sleep and the brain is deprived of oxygen leading to a variety of health conditions such as heart disease, high blood pressure, diabetes, strokes, and death to name a few. Machines that treat sleep apnea are called Continuous Positive Airway Pressure ("CPAP") machines.

These machines provide a continuous flow of air under adjustable pressure to a patient through a mask that is generally sealed by a silicone cushion or seal against the face, secured in place with head gear, creating a pressurized system which provides in essence, a pneumatic splint which in turn depresses the tongue and clears the airway, keeping the airway open, allowing the patient to breath normally. CPAP machines have been shown to significantly reduce the morbidity rates of at risk patients and increase the correspondent health of the patient.

From an online article http://www.medicaldaily.com/sleep-apnea-may-increase-pneumonia-risk-cpap-may-increase-pulmonary-aspiration-bacteria-270464, CPAP machines although being the "gold standard" of treatment for sleep apnea, could be increasing the risk of lung infection. According to a study published in the Canadian Medical Association Journal, the use of a CPAP machine can be a significant source of bacterial, mold, fungi, virus and other microorganisms and is thought to present a high risk of pneumonia. Chang S C, Chen T J, Chen Y M, et al. Sleep apnea and risk of pneumonia: a nationwide population-based study. CMAJ. 2014.

Various methods have been suggested to clean CPAP equipment (masks, tubing and humidifiers) including soap and water, plain water, vinegar, disinfectants and ozone. The Tornado by CPAP Guardian https://www.youtube.com/watch?v=IfTYfoo8C18 is a small ozone generator that requires the user to place the ozone machine into a large container while connecting the ventilator CPAP tubing to the CPAP machine and placing the whole assembly inside a container.

This presents challenges for the user. First, the chamber is very large and cumbersome. Secondly, the entire CPAP machine which contains mostly plastic components and electrical components which can easily oxidize under the exposure to ozone. AG Industries markets a hanging system that is recommended for the CPAP tubing after washing. The hanging system includes a series of mounts, brackets, plugs and clips as required by the user. This system represents another cumbersome invention which is not practical for the everyday CPAP user. The above two products are bulky and cumbersome to use and are not easily hidden, concealed or stored by the user.

U.S. Pat. No. 9,616,147 (So-Clean) by Leva describes sanitizing a CPAP machine comprising steps of connecting a connector unit between a hose and a water reservoir of the CPAP machine with a free end of the connector unit in fluid communication with the water reservoir. U.S. Pat. No. 9,669,124 claims "a connector unit configured to fluidly couple at a proximal end to the medical device".

U.S. Pat. No. 9,610,373 teaches distributing ozone gas into a passageway of the medical instrument, essentially connecting an ozone generator to a CPAP machine. U.S. Pat. No. 9,358,316 teaches a "continuous positive airway pressure connector unit connecting the ozone sanitizing device having an ozone operating system to a continuous positive airway pressure device having a hose and a water reservoir", again connecting an ozone generator with intimate contact to multiple locations directly on the CPAP machines. The above patents generally refer to a closed loop system.

U.S. Patent Publication No. 2016/0250366 teaches "a means for distributing the ozone throughout a gas environment in the medical instrument", again emphasizing the distribution of the ozone gas through the CPAP machine.

The So-Clean, an ozone generator system by Leva, has recently been commercialized and relates primarily a closed loop system connected directly to a CPAP machine and or its accessories including the humidifier. Once again, the prior art is a bulky product that is not easy to store and can be very difficult to connect to the CPAP machine. Further, the user is instructed to modify the CPAP water chamber which can be difficult. Further, when using So-Clean, expensive adaptors are required to fit the unit to a particular CPAP machine model. For the dealer carrying the So-Clean, he or she may have to inventory up to 9 different connectors for their patients' CPAP machines, thereby consuming valuable inventory space, as well as the time required to manage the many inventory parts required on this machine. This also adds additional cost to the patient.

Another problem of the So-Clean device is that the ozone generator contains a pump that pumps ozone from the bottom of the mask chamber through the distribution line into the humidity chamber and returns this gas in a "closed loop" system back to the mask chamber. However, the CPAP machine is not a sealed device. There is an air inlet to the machine that is open to the atmosphere and the pressurized ozone from the So-Clean device will leak into the atmosphere out of the air inlet once the CPAP machine is pressurized by the ozone pump.

Since the So-Clean device requires direct connection to the CPAP machine, there are problems with oxidization of plastic and electronic parts within the CPAP machine. It has been reported that CPAP machine manufacturers will not honor warranty repairs if they discover patients use the prior art on the OEM CPAP machines. The So-Clean device generates approximately 60 mg of ozone per hour and generates approximately 1.7 parts per million of ozone within the sanitizing housing.

The VirtuClean™ by Virtuox is another ozone machine that can be used for the disinfection of CPAP tubing, masks and humidifiers. This device entails a small ozone generator which connects to a CPAP tube and the user places the connected mask into a small zipper bag and partially closes the bag while the machine generates ozone. The problem with this device is that the ozone again leaks into the atmosphere.

If a user wants to sanitize their humidifier, they are instructed to leave the humidifier installed in the CPAP machine and connect the ozone generator via the CPAP tube to the humidifier and operate the ozone generator. Again, this causes two problems. First, the gas escapes through the air inlet opening of the CPAP machine and leaks into the atmosphere. Second, the ozone flows through the CPAP machine causing degradation of the plastic components such as blowers as well as the electronics, which can lead to failure of the CPAP machine.

There exists a need in the medical market place, particularly with respect to CPAP machines and users, to provide an effective, small, storable, user-friendly disinfecting device for CPAP masks, tubing and humidifiers without ruining the CPAP machine and at the same time, minimizing ozone leakage into the environment. The present invention is a device that accomplishes these necessary functions for users of the device.

SUMMARY OF THE INVENTION

An embodiment of the invention is directed to a CPAP equipment sanitizing system that includes an oxidizing gas generator, a sanitizing chamber and tubing. The oxidizing gas generator has an outlet port. The sanitizing chamber includes an enclosure, a fitting and a closure mechanism. The enclosure has an opening. The enclosure is adapted to receive CPAP equipment. The enclosure has an aperture formed in a surface thereof. The fitting extends through the aperture and sealingly engages the sanitizing chamber. The closure mechanism is capable of substantially closing the opening. The tubing operably attaches the outlet port on the oxidizing gas generator and the fitting.

Another embodiment of the invention is directed to a method of sanitizing CPAP equipment comprising. A sanitizing chamber is provided that includes an enclosure, a fitting and a closure mechanism. The enclosure has an opening. The enclosure has an aperture formed in a surface thereof. The fitting extends through the aperture and sealingly engages the sanitizing chamber. An oxidizing gas generator having an outlet port is provided. The fitting is operably attached to the outlet port with tubing. CPAP equipment is placed in the enclosure. The opening is substantially closed with the closure mechanism. Oxidizing gas is generated with the oxidizing gas generator. The oxidizing gas flows through the tubing and into the sanitizing chamber to sanitize an interior of the tubing and the CPAP equipment.

Another embodiment of the invention is directed to a CPAP equipment sanitizing system that includes an oxidizing gas generator, a sanitizing chamber and tubing. The oxidizing gas generator has an outlet port. The sanitizing chamber includes an enclosure, a fitting and a closure mechanism. The enclosure has an opening. The enclosure is adapted to receive CPAP equipment. The enclosure has an aperture formed in a surface thereof. The fitting extends through the aperture and sealingly engages the sanitizing chamber. The fitting includes an inner fitting portion and an outer fitting portion. The inner fitting portion is attached to the sanitizing chamber. The inner fitting portion includes an inner fitting cylindrical section and an inner fitting flange section that outwardly extends from the inner fitting cylindrical section. The outer fitting portion is attached to the inner fitting portion. The tubing attaches to the outer fitting portion. The outer fitting portion includes an outer fitting cylindrical section and an outer fitting flange section that outwardly extends from the outer fitting cylindrical section. The outer fitting section is attached to the inner fitting portion by the inner fitting cylindrical section engaging the outer fitting cylindrical section. The closure mechanism is capable of substantially closing the opening. The tubing operably attaches the outlet port on the oxidizing gas generator and the fitting.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE INVENTION

Figure 1:
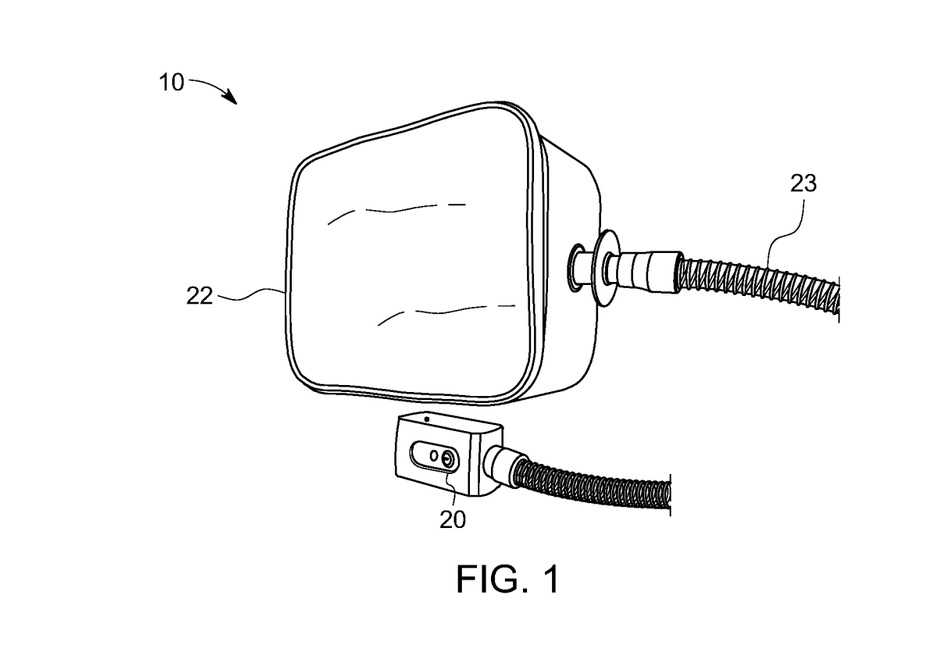
FIG. 1 is a perspective view of a CPAP equipment sanitizing system according to an embodiment of the invention where the CPAP equipment sanitizing equipment includes an oxidizing gas generator, a sanitizing and tubing.

The present invention is directed to a CPAP equipment sanitizing system as illustrated at 10 in FIG. 1. The CPAP equipment sanitizing system 10 includes an oxidizing gas generator 20, a sanitizing chamber 22 and tubing 23.

Figure 2:
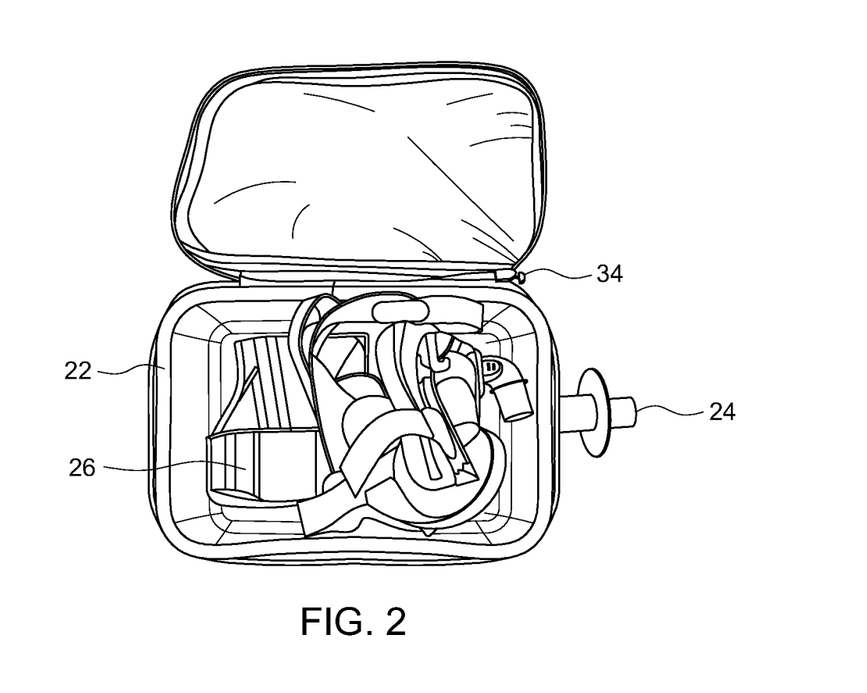
FIG. 2 is a top view of CPAP equipment in the sanitizing chamber where the sanitizing chamber is in an open configuration.

When operated, CPAP equipment 26 that is placed in the sanitizing chamber 22, as illustrated in FIG. 2, may be sanitized with ozone emitted from the oxidizing gas generator 20 using a convenient and easy to use process that is discussed in more detail herein.

Figure 3:
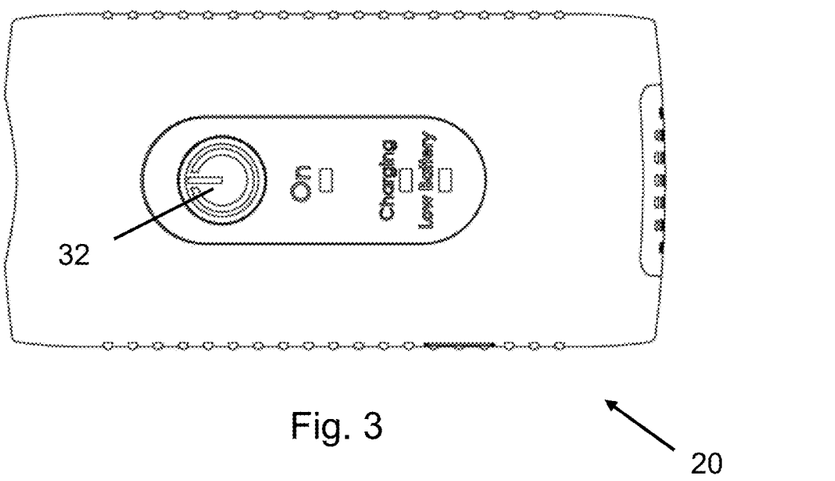
FIG. 3 is a top view of the oxidizing gas generator according to an embodiment of the invention.
Figure 4:
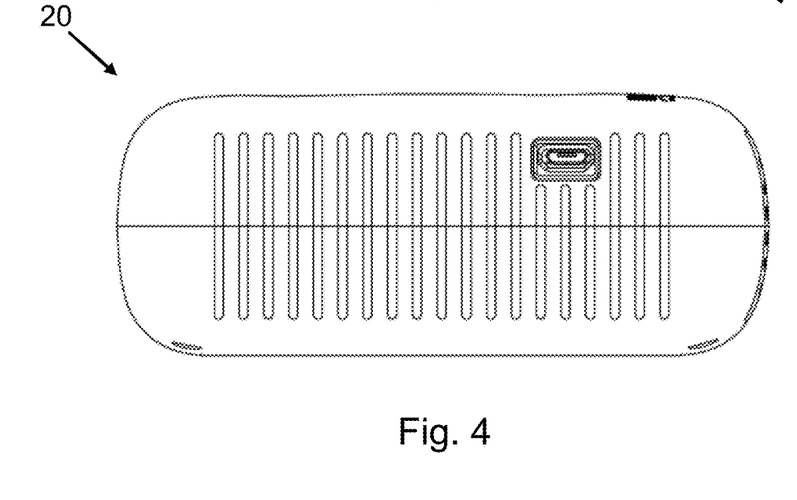
FIG. 4 is a side view of the oxidizing gas generator of FIG. 3.
Figure 5:
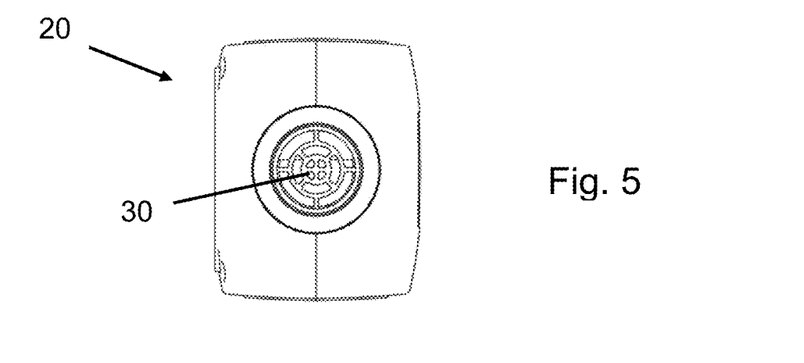
FIG. 5 is an end view of the oxidizing gas generator of FIG. 3.

The oxidizing gas generator 20, which is illustrated in FIGS. 3-5, contains a gas generator module (not shown) that is capable of generating an oxidizing gas such as ozone. A person of skill in the art will appreciate that a variety of components may be used to generate the oxidizing gas. A person of skill in the art will also appreciate that it is possible to use alternative oxidizing gases that are capable of sanitizing the CPAP equipment 26.

The oxidizing gas generator 20 includes an oxidizing gas outlet port 30 through which the oxidizing gas is discharged. The oxidizing gas outlet port 30 may be adapted to use in conjunction with the connectors conventionally used at the ends of tubing used in CPAPs.

The oxidizing gas generator 20 may be operated by a DC battery or AC current of approximately 2,000-3,000 milli ampere hours. Using the batteries (not shown) enhances the portability of the CPAP equipment sanitizing system 10. The batteries are mounted within the oxidizing gas generator 20.

In certain embodiments, the batteries may be replaced when depleted. In other embodiments, the batteries may be rechargeable.

The oxidizing gas generator 20 includes at least one control 32. In certain configurations, the control 30 is a single button on the surface of the oxidizing gas generator 20. Pressing the control 32 causes the oxidizing gas generator 20 to turn on. Pressing the control 32 while the oxidizing gas generator 20 is operating causes the oxidizing gas generator 20 to turn off.

The oxidizing gas generator 20 may include the ability to select the duration at which the oxidizing gas generator 20 will continue to operate after the control 30 is pressed to ensure that the oxidizing gas is emitted for a sufficient time to sanitize the CPAP equipment placed therein.

In certain embodiments, the oxidizing gas generator 20 provides around 10-20 milligrams of ozone output per hour. However, within a similar size chamber, the present invention is able to provide about 1.0-2.0 parts per million to a sanitizing chamber 22 that is approximately 50-165 cubic inches. This concentration equates to about 0.0103 (1.7 parts per million/165 cubic inch) parts per million per cubic inch of sanitizing gas within a sanitizing chamber 22 for every 10-20 milligrams of ozone generated per hour from the oxidizing gas generator 20 and may provide about 0.03 parts per million/cubic inch of ozone (1.7 parts per million/50 cubic inch).

The oxidizing gas generator 20 may further provide 0.005 parts per million to 0.02 parts per million per cubic inch of volume within the sanitizing chamber 22 (1.0 parts per million/50 cubic inch to 1.0 parts per million/2,000 cubic inch). The oxidizing gas generator 20 uses less than 60 milligrams of ozone per hour to create around 1-3 parts per million of ozone in a sanitization chamber 22 for a period of time from around 1 minute to 60 minutes.

Figure 6:
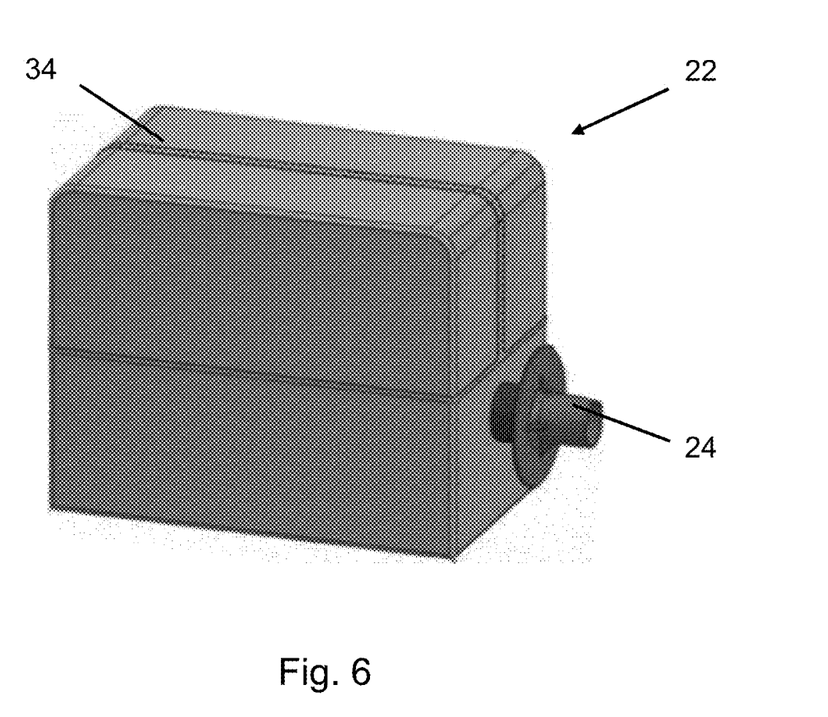
FIG. 6 is a perspective view of the sanitizing chamber according to an embodiment of the invention.

The sanitizing chamber 22 may be flexible, rigid or semi-rigid. The sanitizing chamber 22 may be constructed of the following material but not limited to stainless steel, carbon steel, aluminum, titanium, cotton, rayon, polyolefin, polyamide, polysulfone, nylon, polyester, activated carbon impregnated material, cellulose acetate butyrate, Teflon, woven and or non-woven material.

The sanitizing chamber 22 has an enclosure with an opening therein. The enclosure may be formed in different sizes depending on the CPAP equipment that is intended to be placed therein. For example, if the CPAP equipment includes a humidifying chamber, a large enclosure is needed as compared to if the CPAP equipment does not include the humidifying chamber. The volume of the enclosure may range from approximately 165 cubic inches to more than 3,000 cubic inches.

The sanitizing chamber 22 further includes a closure mechanism 34 such as a zipper to close the opening and enclose the CPAP equipment 26 such as a mask, humidifier or both for processing. Another suitable device that may be used as the closure mechanism 34 is a hook and loop fastener.

Because of the closure mechanism 34 and the material used to fabricate the sanitizing chamber, the invention shows less leakage of ozone into the environment than CPAP equipment sanitizers currently on the market. Using less than 60 milligrams ozone per hour to create about 1.7 parts per million in a certain size sanitizing chamber 22 with there being a pressure drop across the sanitizing chamber 22 of about 0.18-1.3 inches of water at about 50-200 SCFM.

The sanitizing chamber 22 may include at least one divider (not shown) on an interior thereof that facilitates organization of the CPAP equipment placed therein. A surface of the sanitizing chamber 22 may include at least one of text and images (not shown) to let the person using the CPAP equipment sanitizing system 10 to know where the CPAP components are to be placed in the sanitizing chamber 22. In certain embodiments, the at least one of text and images are place on a lower surface inside of the sanitizing chamber 22.

A fitting 24 extends through an aperture in the sanitizing chamber 22. The sanitizing chamber 22 is substantially sealed around the fitting 24. As used herein, substantially sealed means that the oxidizing gas is prevented from flowing out of the sanitizing chamber 22 by passing between the fitting 24 and the sanitizing chamber 24. The fitting 24 may be rigid or flexible. Examples of material from which the rigid fitting 24 may be fabricated include steel or moldable plastic suitable for the application. Examples of material from which the flexible fitting 24 could be manufactured include rubber, thermoplastic elastomer (TPE), nylon, polycarbonate, acrylic, polypropylene, polyamide, Teflon or other suitable materials.

The invention contains various means of securing the fitting 24 to the sanitizing chamber 22 and provides a robust attachment of the fitting 24 to the sanitizing chamber 22. The fitting 24 of the present invention provide a means to couple the generator 20 of oxidizing gas such ozone with conduit such as CPAP or ventilator tubing to the sanitizing chamber 22 whereby the conduit does not make direct contact with contained articles.

Figure 8:
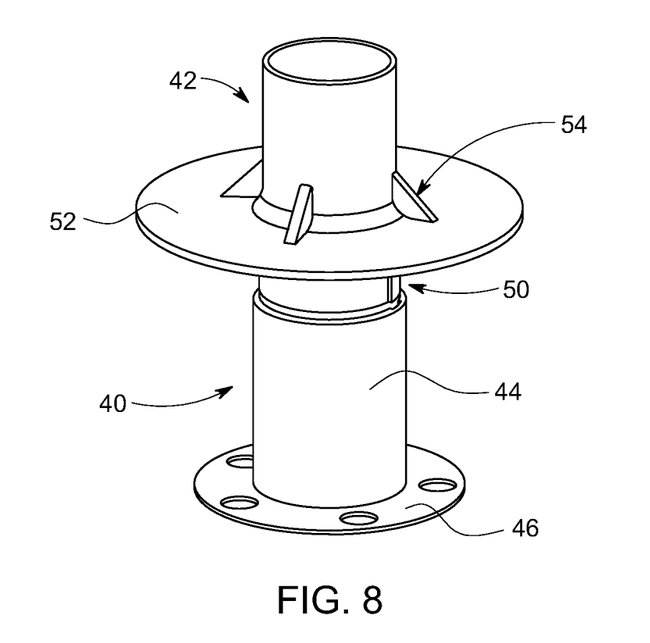
FIG. 8 is a perspective view of a fitting for the sanitizing chamber illustrated in FIG. 6.

FIG. 6 illustrates the sanitizing chamber 22 with the fitting 24. FIG. 8 is a perspective view of the fitting 24. The fitting 24 includes an inner fitting portion 40 and an outer fitting portion 42. While it is illustrated that the fitting 24 includes two parts, it is possible for the fitting 24 to be formed in one part or in more than two parts.

Figure 9:
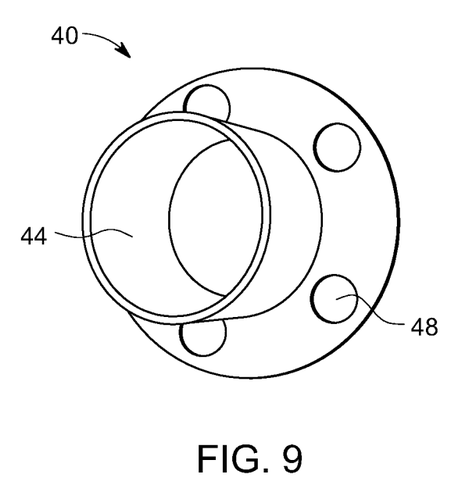
FIG. 9 is an upper perspective view of an inner portion of the fitting.
Figure 10:
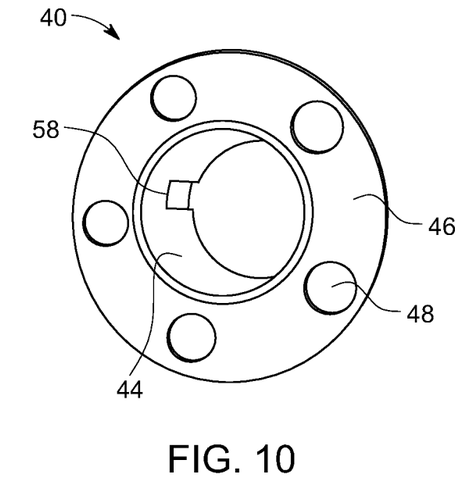
FIG. 10 is a lower perspective view of the inner portion of the fitting.

The inner fitting portion 40, which is illustrated in FIGS. 9 and 10, generally includes a cylindrical section 44 and a flange section 46 that outwardly extends from the cylindrical section 44 proximate an end thereof.

An inner surface of the cylindrical section 44 may have at least one indent 58 formed therein that is adapted to receive a complementarily formed extension on an outer surface of the outer fitting portion 42 to facilitate retaining the inner fitting portion 40 in engagement with respect to the outer fitting portion 42. Conversely, the inner fitting portion 42 may contain one or more extension that fit into one or more corresponding notches in the outer fitting portion 42.

The flange section 46 is secured to the sanitizing container 22 as is described in more detail herein. The flange section 46 may have a generally circular profile at an outer surface thereof.

The flange section 46 has a width that is sufficiently wide to facilitate forming a strong bond between the inner fitting portion 40 and the material of the sanitizing chamber 22. In certain embodiments, the width of the flange section 46 is at least 50 percent of a diameter of the cylindrical section 44.

The flange section 46 may have at least one aperture 48 formed therein. In certain embodiments, the flange section 46 has a plurality of apertures 48 formed therein. The apertures 48 facilitate bonding of the material on opposite sides of the flange section 46 to reduce the potential of the inner fitting portion 40 moving with respect to the material.

The outer fitting portion 42 includes a cylindrical section 50 and a flange section 52 that outwardly extends from the cylindrical section 50. The cylindrical section 50 has an outer diameter that is less than the inner diameter of the cylindrical section 44 so that a portion of the cylindrical section 50 may be extended into the cylindrical section 50.

The flange section 52 is positioned intermediate opposite ends of the cylindrical section 50. In certain embodiments, the flange section 52 is oriented substantially perpendicular to the cylindrical portion 50. The flange section 52 may have a generally circular profile at an outer surface thereof.

The flange section 52 has a width that is sufficiently wide to facilitate a person to place his/her fingers on opposite sides of the cylindrical section 50 to prevent the outer fitting portion 42 from moving when attaching tubing to the outer fitting portion 42 or detaching the tubing from the outer fitting portion 42. In certain embodiments, a diameter of the flange section 52 is at least 30 percent larger than a diameter of the cylindrical section 50. In other embodiments, the diameter of the flange section 52 is between about 60 percent and about 100 percent larger than the diameter of the cylindrical section 50.

The flange section 52 should resist deformation when attaching or detaching the tubing to the outer fitting member 42. The strength of the flange section 52 may be enhanced with at least one support rib 54 that extends between the cylindrical section 50 and the flange section 52.

Figure 7:
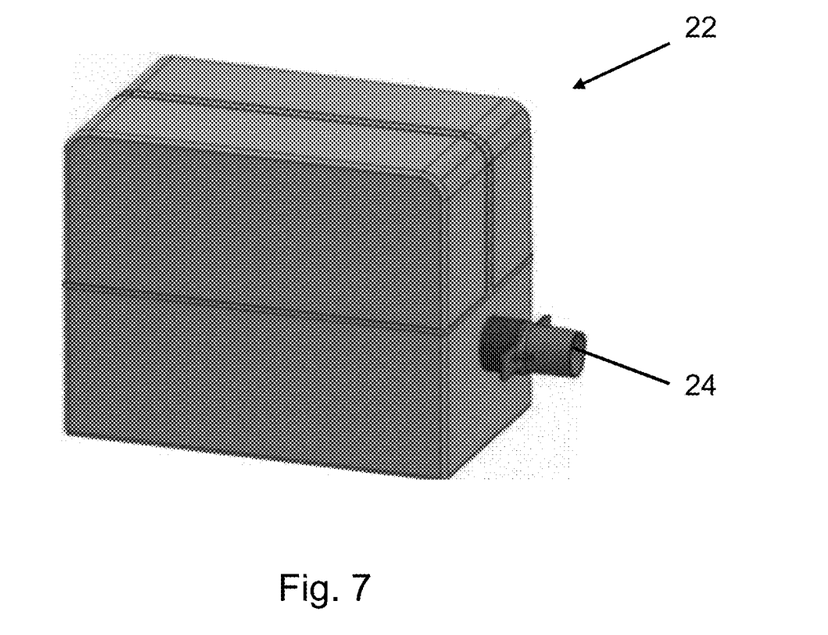
FIG. 7 is a perspective view of an alternative embodiment of the sanitizing chamber.

In another configuration, which is illustrated in FIG. 7, the outer fitting portion includes two outwardly extending tabs 56 as opposed to the circular flange section 52 illustrated in FIG. 6. Otherwise, the outwardly extending tabs 56 have similar features to the circular flange section 52 illustrated in FIG. 6.

The fitting 24 is coupled to the sanitizing chamber 22 such as a bag using one or multiple layers of material. The fitting 24 may be attached by sewing, ultra-sonic welding, solvent bonding, gluing, or RF welding and is not limited to these methods of attachments as other methods may be contemplated for the purpose of the invention.

Figure 11:
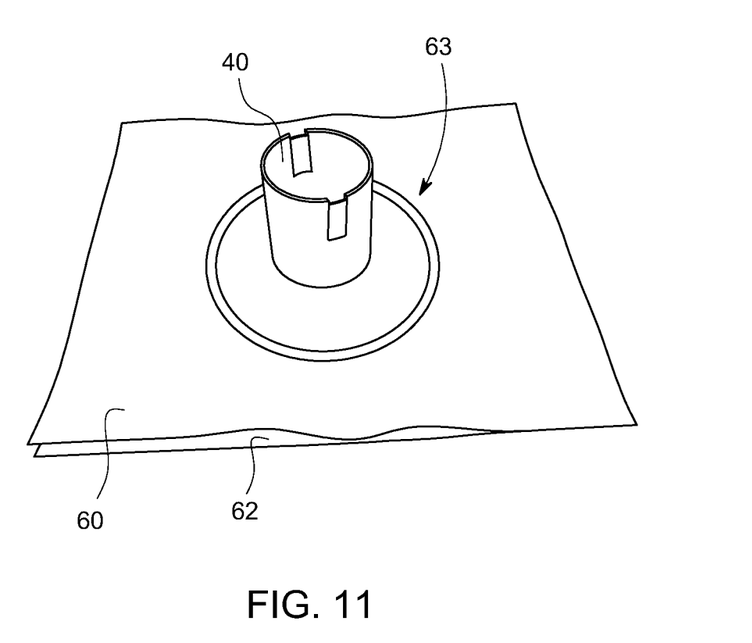
FIG. 11 is an upper perspective view of the inner portion of the fitting attached to material for the sanitizing chamber.
Figure 12:
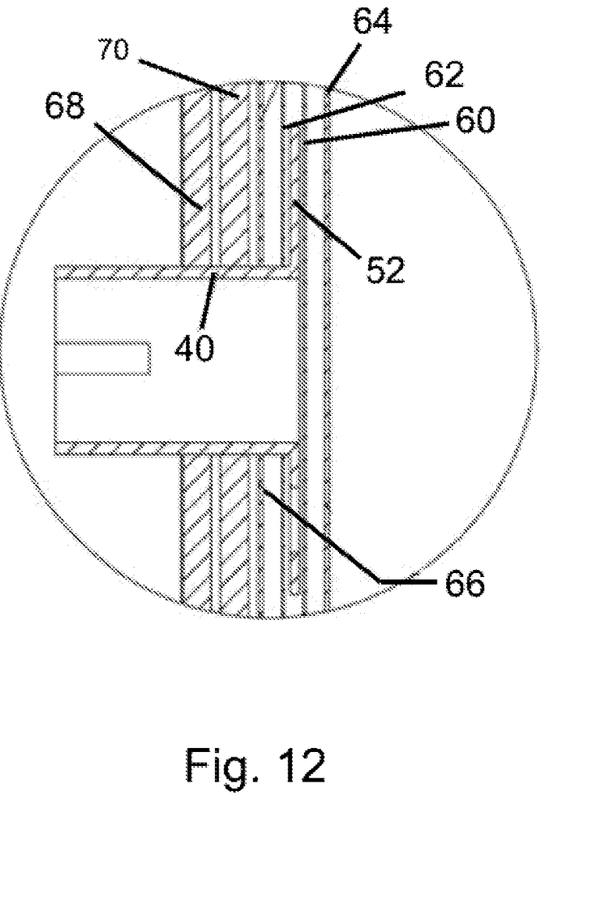
FIG. 12 is a sectional view of the inner portion of the fitting attached to the material for the sanitizing chamber.

To minimize the potential of the inner fitting portion 40 becoming dislodged from the sanitizing container 22, a multi-layer structure may be used such as illustrated in FIG. 12. Inner layers 60, 62 are placed along opposite sides of the flange section 46. The inner layers 60, 62 are secured to the flange section 46. Examples of techniques that may be used to secure the inner layers 60, 62 to the flange section 46 include adhesives, heat-sealing, RF welding or sonic welding. FIG. 11 illustrates a circularly shaped heat-seal 63. The heat-seal may be positioned around the flange section 46 or the heat-seal may be at least partially over the flange section 46. As referenced above, the apertures 48 may be used to facilitate forming a strong bond between the inner layers 60, 62. In certain embodiments, the inner layers 60, 62 are fabricated from a vinyl material.

Intermediate layers 64, 66 are placed along surfaces of the inner layers 60, 62 that are opposite the flange section 46. The intermediate layers 64, 66 may be secured to each other, which thereby secure the inner layers 60, 62 and the flange section 46 using a variety of techniques. An example of one suitable technique for securing the intermediate layers 64, 66 is sewing.

On the outwardly facing intermediate layer 66, an outer protective layer 68 is applied. The outer protective layer 68 is visible from the outside of the sanitizing chamber 22. As such, the outer protective layer 68 may have a color and/or a pattern on the surface thereof that enhances the aesthetics of the sanitizing chamber 22. An example of one material that may be use for the outer protective layer 68 is polyester. A foam layer 70 may be positioned between the outer protective layer 68 and the outwardly facing intermediate layer 66.

Figure 13:
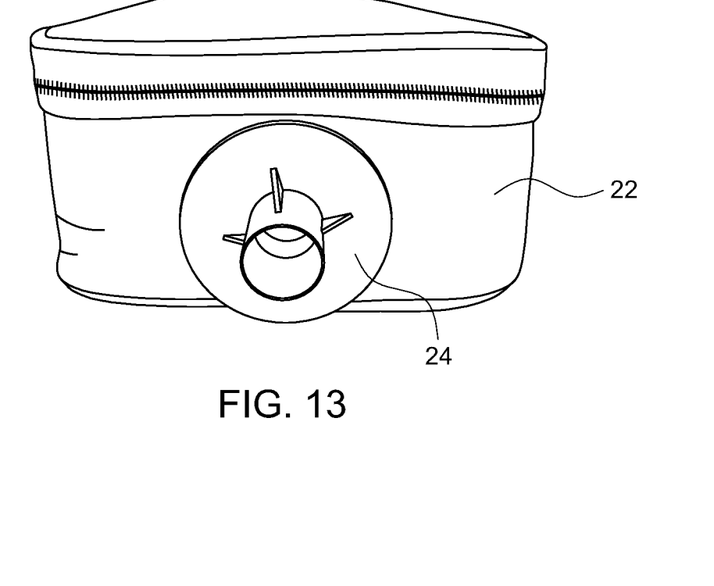
FIG. 13 is an end view of the sanitizing chamber illustrating attachment of the fitting to the sanitizing chamber.

The fitting 24 attached to the side of the sanitizing chamber 22 is illustrated in FIG. 13. A person of skill in the art will appreciate that the fitting 24 may be attached to other areas of the sanitizing chamber 22.

Figure 14:
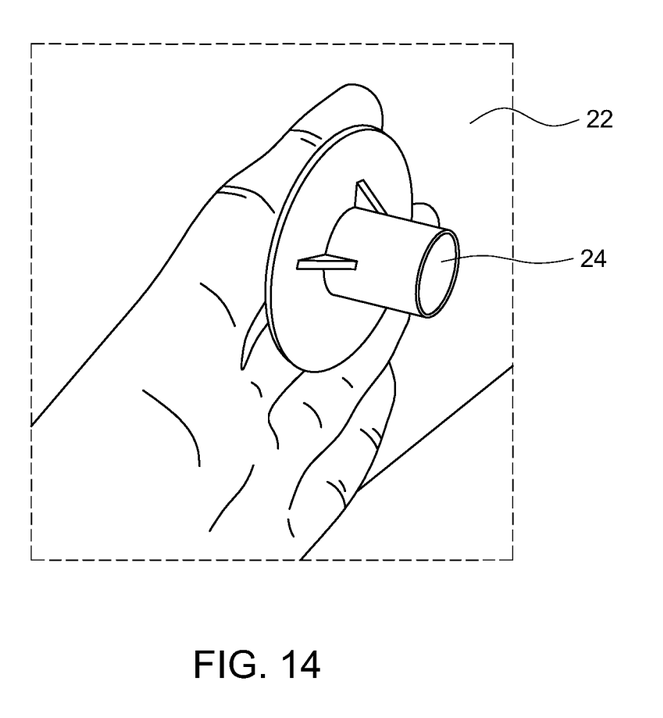
FIG. 14 is a perspective view of a person grasping the fitting on the sanitizing chamber.
Figure 15:
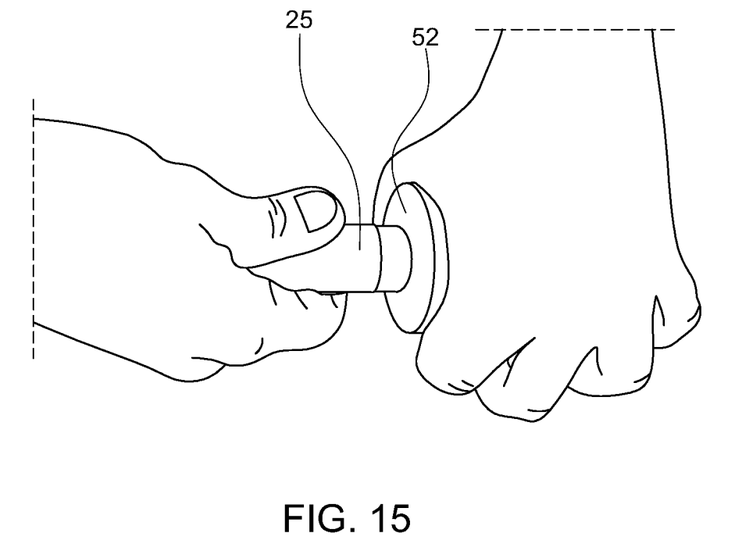
FIG. 15 is a top view of tubing being attached to the sanitizing chamber while the person is grasping the fitting.

The fitting 24 thereby provides a means of attaching a ventilation tube or CPAP tube from the oxidizing gas generator 20 to the sanitizing chamber 22 with a flexible or semi-flexible member by placing at least one digit of a hand on the underside of the flange section 52, as illustrated in FIG. 14, and holding the tubing 23 with another hand and bringing the tubing 23 and the fitting 24 together in a secure connection as illustrated in FIG. 15. A secure connection defined as a connection suitable to enable oxidizing gas to be delivered from the oxidizing gas generator 20 to the inside articles located inside the sanitizing chamber 22.

Figure 16:
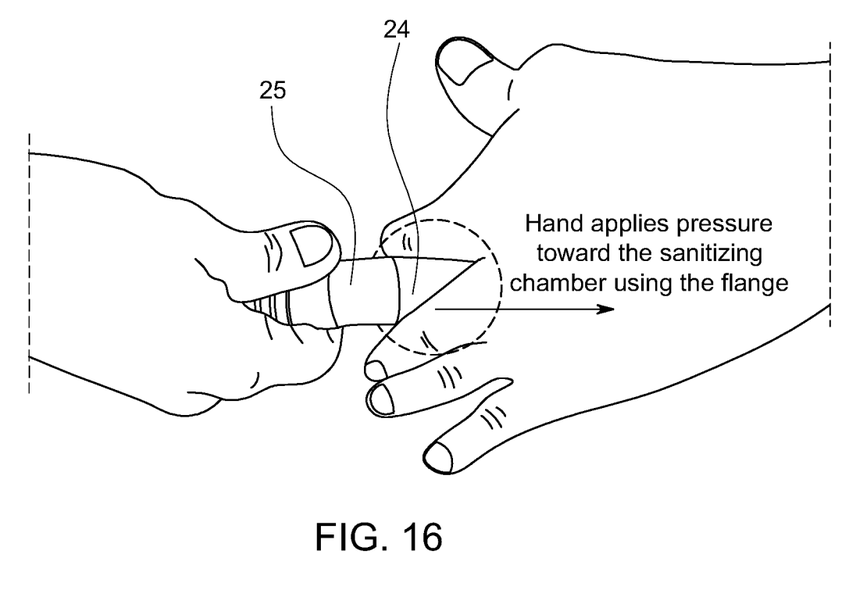
FIG. 16 is a top view of the tubing being detached from the sanitizing chamber while the person is grasping the fitting.

When it is desired to detach the tubing 23 from the fitting 24, the user places a first hand on a side of the flange section 52 that is opposite the sanitizing chamber 22 as illustrated in FIG. 16. A second hand grasps the connector 25 at the end of the tubing 23 and urges the tubing 23 away from the fitting 24. The flange section 52 thereby enhances the ability to detach the tubing 23 from the sanitizing chamber 22 as compared to prior art CPAP equipment sanitizing systems.

Each cited prior art has relied upon the ozone generator maintaining a direct connection of a conduit to either the CPAP mask, humidifier or CPAP machine or all three to maintain a given concentration of oxidative gas within the article of sanitization (i.e. mask and humidifier).

This invention is able to maintain a level of ozone within the sanitizing chamber 22 and/or CPAP mask without having directly connected the oxidizing gas generator 20 to the article being sanitized. The level of ozone within the articles can be within 0.4 parts per million to 20 parts per million, or more preferably from around 1.0 parts per million to 3.0 parts per million for a period of time.

With this invention, the CPAP mask and/or humidifier is able to subject the articles for sanitization to a sanitizing force (i.e. gas or light) without having to traverse a tube across a wall of the sanitizing chamber 22.

There are approximately 20 million Americans who suffer from sleep apnea. There are approximately 4-5 million patients who currently receive CPAP therapy from a CPAP machine. Many of these patients are elderly, immunocompromised, arthritic and weak. One of the problems that a CPAP user faces especially the elderly and the arthritic is pain in the hands and in particular the knuckles when attaching and detaching CPAP tubing which generally contains a vinyl sheet extruded around a helical supportive structure.

Conventionally, a standard ISO 22 millimeter female connector is provided at opposite ends of the CPAP tubing. This connector fits over a 22 millimeter male connector located on the outlet side a CPAP machine. In general, CPAP tubing is attached and detached from CPAP equipment using the fingertips alone putting pressure on the knuckles.

The force to attach or detach the CPAP tubing from the CPAP machine can be quite considerable. In fact, forces of up to 30 pounds can be required to attach and detach a CPAP tube from related equipment. This is an extreme amount of force required to be generated by someone who is weak, suffers from painful arthritic joints and other illnesses.

The force needed to attach and detach the CPAP tubing to the CPAP machine causes pressure points on the hand. The connectors on the CPAP tubing and the CPAP machine need to provide sufficient friction to prevent the CPAP tubing from inadvertently disengaging from the CPAP machine. This engagement may be particularly burdensome to elderly persons and/or persons with arthritis in their hands Sometimes people who suffer from pain, arthritis and weakness will try to disengage the CPAP tubing from the CPAP machine by grasping the tubing as opposed to the connector at the end of the CPAP tubing. Pulling on the CPAP tubing can lead to damage or degradation of the CPAP tubing.

This invention overcomes these problems associated with having to pinch and squeeze finger tips together to remove rubber cuffed tubing from medical equipment. The present invention allows the user to hold the fitting 24 associated with the sanitizing chamber 22 in their hand and a portion of their palm with extended finger tips using a large surface area of soft tissue, muscle and bones, thereby allowing the user to increase the leverage from his or her hand and reduce the pin pointed of the stress on their knuckles, joints and finger tips.

FIG. 14 shows the portion of the fitting 24 that may be easily held with the finger tips and the bottom portion of the hand as opposed to pinching with the thumb and index finger. The fitting 24 allows the user to generate maximum leverage to remove and attach tubing to a sanitizing chamber 22 or other medical equipment, using the not only the fingers but by allowing the user to engage part of the palm. Further, the flange section 52 alleviates pain by providing another means than just using compression of the digits (forefinger and thumb) together and allows the user to merely hold the fitting 24 with relaxed, extended fingers.

There is only a resistance by the hand and lower extremity as opposed to small portions of finger digits. Further, upon detachment, again the user is not required to pinch or squeeze a fitting and hold the fitting while the rubber cuff is removed from the connector. The force required by using only the thumb and forefinger can be painful to the user's joints.

The fitting 24 with the flange section 52 extending therefrom may also be attached to the CPAP tubing connector 25 as well to be used as an alternative means of attaching and detaching CPAP tubing to medical equipment.

The forces required to apply and attach and detach CPAP tubing from associated fittings are as high as 30 pounds. This force can be destructive to flexible side walls of structures. Heretofore, there has been no means to be able to repeatedly employ such high forces to a flexible wall of a sanitizing chamber 22 without damaging the sanitizing chamber 22 or causing deformation to the side walls or crumpling of a soft, flexible sanitizing chamber 22. The invention allows the user to repeatedly over the course of years, attach and detach between uses, medical tubing from the sanitizing chamber 22 without damaging, crumpling or deforming the side walls or wall or portion of a wall with the sanitizing chamber 22.

The fitting 24 may further be comprised of a straight or tapered member protruding from the base which allows the user to connect the fitting 24 to a tube which in turn is connected to the oxidizing gas generator 20. The length of the straight or tapered fitting is at least as long as the dimension of the inner diameter of the base of the tube. The inner diameter of the fitting 24 may be as small as about 0.100 inches and as large as 4 inches and the length of the fitting 24 may be as long as about 6 inches. The volume of internal inner diameter of the fitting 24 could range from about 0.0039 cubic inches to about 75 cubic inches.

The present invention offers an easy method to sanitize medical and other equipment and articles of use without having to connect the oxidizing gas generator 20 directly to the articles.

Previously mentioned prior art CPAP disinfection units (Leva, VirtuClean, Tornado) force the user to connect their oxidizing gas generator 20 via a CPAP tube directly to a CPAP machine's 22 millimeter male connection which is in turn, sealed to the CPAP humidity chamber. This is the only way to distribute ozone into the humidity chambers via the prior art.

FIG. 2 illustrates how a humidity chamber 72 fits freely in the sanitizing chamber 22 without connecting the humidity chamber to a CPAP tube. Since the present invention is free from bulky manifolds within the open sanitizing chamber, it allows for an easy fit of the CPAP humidity chamber 72 within the sanitizing chamber 22. The sanitizing chamber 22 may be large enough to accommodate both a CPAP mask and CPAP humidity chamber. The sanitizing chamber 22 may be collapsed or reduced in size for storage purposes.

Further, the present invention provides a means to sanitize CPAP equipment and supplies without pumping ozone and other oxidative gases through sensitive CPAP machines and their associated components and electronics. The method may include a pressure drop across the sanitizing chamber.

The present invention may further incorporate an activated carbon or other type of oxidative gas adsorbent material on the inlet side of the oxidizing gas generator 20. When the disinfection cycle is complete, a fan (not shown) in the oxidizing gas generator 20 may reverse directions and draw gas out of the sanitizing chamber 22 and remove the oxidative gas. The filter has an associated pressure drop and fitting size.

The present invention may also incorporate an absorbent or adsorbent filter or filter material within the chamber. The chamber provides a means to secure the filter or filter material to the inside of the chamber.

CPAP machines require CPAP tubing that connect the CPAP machine to the patient CPAP mask. The air is pressurized by a motor within the CPAP machine and directed out of the humidity chamber where the CPAP tubing is connected to the patient mask. Historically, the CPAP tubing is manufactured as standard 6 foot long hose with rubber cuffs.

More recently, due to the aftermarket sales volume that CPAP machine manufacturers wish to retain for consumable items such as tubing, CPAP machines today are made with increasingly proprietary fittings on the machine end which accept heated tubes.

Additionally, heated tubes are a benefit to patients in that they retain the water in vapor form as it leaves the humidity chamber, preventing condensation from occurring on the patient's face and or nose. Often, these heated tubing fittings are patented and come in a variety of different inside diameters and are not universally compatible from one machine manufacturer to another.

Figure 17:
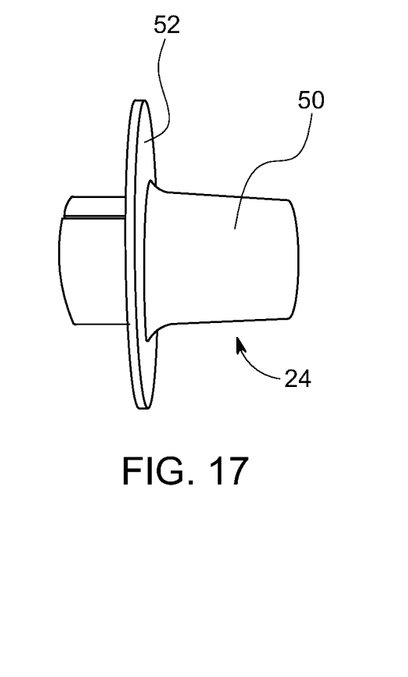
FIG. 17 is a side view of the fitting where an outer surface of the cylindrical section is tapered.

One further advantage of the invention is that it is manufactured with a novel one size fits all universal fitting 24 and will accept any CPAP tubing connector of varying inner diameters. An outer surface of the cylindrical section 50 may be tapered so that an outer diameter of the cylindrical section 50 is wider proximate the flange section 52 that at a distal end of the cylindrical section 50 as illustrated in FIG. 17.

In certain embodiments, proximate the flange section 52, the diameter of the outer surface may be about 0.90 inches and proximate the distal end of the cylindrical section 50, the diameter of the outer surface may be about 0.80 inches. As such, the diameter of the outer surface may be at least 10 percent smaller proximate the flange section than at the distal end of the cylindrical section 50.

Figure 18:
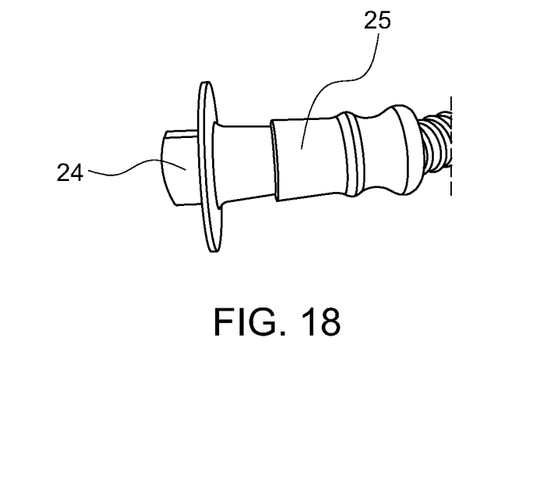
FIG. 18 is a side view of the fitting used in conjunction with tubing having an end connector.
Figure 19:
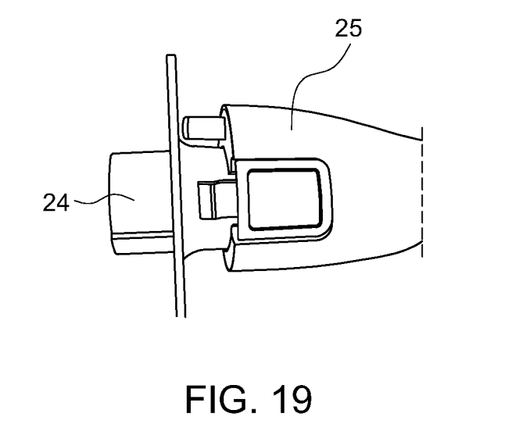
FIG. 19 is a side view of the fitting used in conjunction with tubing having an alternative end connector.
Figure 20:
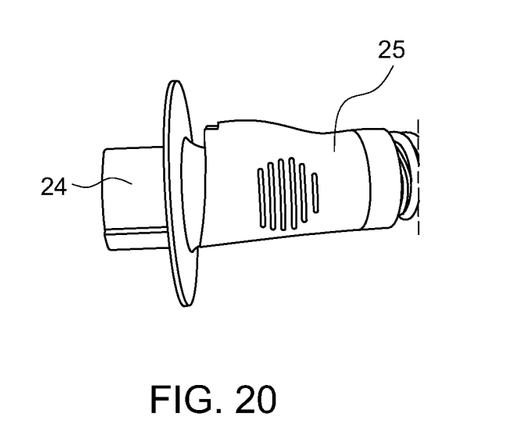
FIG. 20 is a side view of the fitting used in conjunction with tubing having another end connector.

In certain embodiments, the connector 25 is a standard 22 millimeter rubber connector 25 having an inner diameter of approximately 0.85 inches (illustrated in FIG. 18). In other embodiments, a heated tubing connector 25 on the Respironics Dream Station has an inner diameter of approximately 0.88 inches (illustrated in FIG. 19). In still other embodiment, the Fisher Paykel heated tubing connector 25 has an inner diameter of approximately 0.89 inches (illustrated in FIG. 20). The benefits to the customer and the dealers are multifold.

The universal fitting 24 is easy to connect to any CPAP machine hose and requires little effort or thought from the user to connect and seal. Such a configuration is contrary to the prior art CPAP equipment sanitizing systems where it is necessary to the consumer to purchase adapters based upon the type of CPAP equipment that is being used. In certain situations, there are 10 or more adapters from which to select.

Example 1

The present invention was compared to a So-Clean ozone sanitizer. Each unit as placed in an enclosed container to trap ozone that was emitted. The ozone concentration outside of each sanitizing chamber was analyzed. The So-Clean sanitizing machine was allowed to operate and during its cycle the ozone was measured inside the test chamber. The ozone concentration during the operation of the So-Clean unit measured approximately 950 parts per billion.

The present invention was set inside the chamber and allowed to fill the sanitizing chamber. The ozone concentration around the present invention measured approximately 650 parts per billion. This demonstrates that the present invention leaks less ozone into the atmosphere than prior art which uses a more powerful ozone generator (which generates more ozone within a sanitizing chamber).

The ozone velocity through the fitting 24 into the sanitizing chamber 22 is between about 0.010 feet per minute and about 0.040 feet per minute. In other embodiments, the ozone velocity through the fitting 24 into the sanitizing chamber 22 is about 0.023 feet per minute.

Example 2

The present invention was connected to a flow meter. A pressure gauge is installed on the outlet of the flow meter. The flow meter was adjusted to various flow rates and the pressure required to move air through the system was recorded with the zipper closed. The results are set forth below in Table 1: Flow rate is SCFH (standard cubic feet per hour).

TABLE 1

| Flow Rate (SCFM) | Pressure Drop - Small Bag | Pressure Drop - Large Bag |
|---|---|---|
| 50 | 0.27 inches H$_2$O | 0.10 inches H$_2$O |
| 100 | 0.70 inches H$_2$O | 0.27 inches H$_2$O |
| 200 | 1.90 inches H$_2$O | 0.88 inches H$_2$O |

Example 3

The purpose of this test was to measure pressure drop of large and small bag at 30 liters per minute. These sanitizing chambers were used with oxidizing gas generator 20 used for disinfection of CPAP equipment.

The tests are carried out by connecting the sanitizing chamber 22 via the tubing 23 the oxidizing gas generator 20 to below system. The outlet of the vacuum pump connects to a laminar air flow unit that measures the flow accurately down to 10 liters per minute. The flow valve controls the amount of air dispersing into the sanitizing chamber 22. The pressure drop of the sanitizing chamber 22 was measured by an MKS digital transducer. These tests were carried out at 30 liters per minute of air flow.

The large sanitizing chamber 22 showed a pressure drop of about 0.091 inches of water gauge. The pressure drop for the sanitizing chamber 22 was about 0.181 inches of water gauge.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A CPAP equipment sanitizing system comprising:
   an oxidizing gas generator having an outlet port;
   a sanitizing chamber that comprises:
      an enclosure having an opening, wherein the enclosure is adapted to receive CPAP equipment and wherein the enclosure has an aperture formed in a surface thereof;
      a fitting that extends through the aperture and sealingly engages the sanitizing chamber, wherein the fitting comprises:
         an inner fitting portion that is attached to the sanitizing chamber; and
         an outer fitting portion that is attached to the inner fitting portion, wherein the outer fitting portion comprises an outer fitting cylindrical section and an outer fitting flange section that outwardly extends from the outer fitting cylindrical section and wherein a diameter of the outer fitting flange section is between about 60 percent and about 100 percent larger than a diameter of the outer fitting cylindrical section;
      a closure mechanism that is capable of substantially closing the opening; and
      tubing that operably attaches the outlet port on the oxidizing gas generator and the outer fitting cylindrical section.

2. The CPAP equipment sanitizing system of claim 1, wherein the inner fitting portion comprises an inner fitting cylindrical section and an inner fitting flange section that outwardly extends from the inner fitting cylindrical section and wherein the outer fitting cylindrical section is attached to the inner fitting portion by the inner fitting cylindrical section engaging the outer fitting cylindrical section.

3. The CPAP equipment sanitizing system of claim 2, wherein one of the inner fitting cylindrical section and the outer fitting cylindrical section has an extension on a surface thereof, wherein one of the inner fitting cylindrical section and the outer fitting cylindrical section on which the extension is not formed has an indent formed therein and wherein when the inner fitting cylindrical section engages the outer fitting cylindrical section, the extension at least partially seats in the indent.

4. The CPAP equipment sanitizing system of claim 2, wherein the enclosure further comprises;
   a first inner layer and a second inner layer attached to opposite sides of the inner fitting flange section; and
   a first outer layer and a second outer layer attached to a surface of the first inner layer and the second inner layer that is opposite the inner fitting flange section, wherein the first and second inner layers and the first and second outer layers are attached to the sanitizing chamber to mount the fitting with respect to the sanitizing chamber.

5. The CPAP equipment sanitizing system of claim 4, wherein the first and second inner layers are bonded to each other and bonded to the inner fitting flange section and wherein the first and second outer layers are sewn together to cause the first and second inner layers and the inner fitting flange section to be retained between the first and second outer layers.

6. The CPAP equipment sanitizing system of claim 5, wherein the inner fitting flange section has a plurality of apertures formed therein and wherein the first and second inner layers are bonded together in the plurality of apertures.

7. The CPAP equipment sanitizing system of claim 2, wherein the outer fitting cylindrical section has a tapered outer surface so that a diameter of the outer surface proximate the flange section is greater than a diameter of the outer surface proximate a distal end of the outer fitting flange section.

8. The CPAP equipment sanitizing system of claim 1, wherein the oxidizing gas generator is an ozone generator and wherein the tubing comprises a first end and a second end, wherein the first end frictionally engages the outlet portion on the oxidizing gas generator and wherein the second end frictionally engages the fitting.

9. The CPAP equipment sanitizing system of claim 1, wherein at least a portion of the enclosure is fabricated from a flexible material and wherein the closure mechanism is a zipper or a hook and loop fastener.

10. A CPAP equipment sanitizing system comprising:
    an oxidizing gas generator having an outlet port;
    a sanitizing chamber that comprises:
       an enclosure having an opening, wherein the enclosure is adapted to receive CPAP equipment and wherein the enclosure has an aperture formed in a surface thereof;
       a fitting that extends through the aperture and sealingly engages the sanitizing chamber, wherein the fitting comprises:
          an inner fitting portion that is attached to the sanitizing chamber, wherein the inner fitting portion comprises an inner fitting cylindrical section and an inner fitting flange section that outwardly extends from the inner fitting cylindrical section; and
          an outer fitting portion that is attached to the inner fitting portion, wherein the tubing attaches to the outer fitting portion, wherein the outer fitting portion comprises an outer fitting cylindrical section and an outer fitting flange section that outwardly extends from the outer fitting cylindrical section, wherein a diameter of the outer fitting flange section is between about 60 percent and about 100 percent larger than a diameter of the outer fitting cylindrical section and wherein the outer fitting cylindrical section is attached to the inner fitting portion by the inner fitting cylindrical section engaging the outer fitting cylindrical section; and a closure mechanism that is capable of substantially closing the opening; and tubing that operably attaches the outlet port on the oxidizing gas generator and the fitting.

11. The CPAP equipment sanitizing system of claim 10, wherein the inner fitting flange section is used for attaching the flange to the sanitizing chamber.

12. The CPAP equipment sanitizing system of claim 10, wherein the outer fitting cylindrical section has a tapered outer surface proximate a distal end thereof, wherein a diameter of the outer surface proximate the distal end is less than a diameter of the outer surface opposite the distal end.

13. The CPAP equipment sanitizing system of claim 1, wherein a spacing between the outer fitting flange section and the enclosure permits a user to position a finger between the outer fitting flange section and the enclosure.

* * * * *